United States Patent [19]
Kondo

[11] Patent Number: 5,177,021
[45] Date of Patent: Jan. 5, 1993

[54] ELEMENT FOR IMMUNOASSAY AND PROCESS OF USING THE SAME

[75] Inventor: Asaji Kondo, Asaka, Japan

[73] Assignee: Fuji Photo Film Co., Ltd., Kanagawa, Japan

[21] Appl. No.: 25,843

[22] Filed: Mar. 16, 1987

[30] Foreign Application Priority Data

Mar. 17, 1986 [JP] Japan ................... 61-58764

[51] Int. Cl.$^5$ ......................................... G01N 33/543
[52] U.S. Cl. .................................... 436/518; 435/7.92; 435/7.93; 435/7.94; 435/7.95; 435/969; 435/970; 436/535; 436/538; 436/807; 436/808; 436/809; 436/810; 422/56; 422/58; 422/68; 422/99
[58] Field of Search ............... 435/7, 805; 436/518, 436/535, 538, 807–810; 422/56, 58, 68, 99

[56] References Cited

U.S. PATENT DOCUMENTS

| | | | |
|---|---|---|---|
| 3,901,657 | 8/1975 | Lightfoot | 422/56 |
| 4,017,597 | 4/1977 | Reynolds | 436/531 |
| 4,094,647 | 6/1978 | Deutsch et al. | 436/500 |
| 4,234,316 | 11/1980 | Hevey | 435/810 X |
| 4,258,001 | 3/1981 | Pierce et al. | 422/56 |
| 4,361,537 | 11/1982 | Deutsch et al. | 422/56 |
| 4,381,921 | 5/1983 | Pierce et al. | 436/535 |
| 4,387,164 | 6/1983 | Hevey et al. | 422/56 |
| 4,391,904 | 7/1983 | Litman et al. | 435/7 |
| 4,446,232 | 5/1984 | Liotta | 435/7 |
| 4,626,513 | 12/1986 | Burton et al. | 436/518 |
| 4,668,619 | 5/1987 | Greenquist et al. | 435/7 |
| 4,746,631 | 5/1988 | Clagett | 436/514 X |
| 4,803,170 | 2/1989 | Stanton et al. | 436/518 |
| 4,889,816 | 12/1989 | Davis et al. | 436/518 |

FOREIGN PATENT DOCUMENTS

| | | | |
|---|---|---|---|
| 017414 | 10/1980 | European Pat. Off. | 435/810 |
| 0078225 | 5/1983 | European Pat. Off. | 422/56 |
| 111762 | 6/1984 | European Pat. Off. | 436/501 |
| 231830 | 8/1987 | European Pat. Off. | 435/810 |
| 277723 | 8/1988 | European Pat. Off. | 436/518 |
| 2085159 | 4/1982 | United Kingdom | 422/56 |

OTHER PUBLICATIONS

Patent Abstract of Japan, vol. 8, No. 105 (P-274) (1542)—May 17, 1984 & JP 59-15861 Konishiroku Shashin Kogyo K.K.—Jan. 26, 1984.

Primary Examiner—Esther L. Kepplinger
Assistant Examiner—Carol A. Spiegel
Attorney, Agent, or Firm—McAulay Fisher Nissen Goldberg & Kiel

[57] ABSTRACT

A dipping element for immunoassay or quantitative analysis of an immunoreactive analyte is disclosed having a first matrix having a carrier therein containing an immobilized antibody capable of an immunochemical reaction with a sample antigen. The immobilized antibody is not released into the aqueous liquid sample upon contact. The element further comprises a second matrix which contains labelled antigen which does dissolve in the aqueous liquid sample upon contact. On dipping, the marker-labelled antigen reacts with the immobilized antibody in competition with the antigen-antibody reaction between the analyte antigen and the immobilized antibody. if the analyte is an antibody, then the second matrix contains a marker labelled antibody and the first matrix contains an immobilized antigen. Methods for the quantitative analysis of an analyte antigen or antibody are also disclosed.

4 Claims, 3 Drawing Sheets

ELEMENT FOR IMMUNOASSAY AND PROCESS OF USING THE SAME

FIELD OF THE INVENTION

The present invention relates to an element for the immunoassay utilizing a competitive antigen-antibody reaction and a process for the quantitative analysis wherein said element is used. More particularly, it relates to such an immunoassay and a process for the quantitative analysis utilizing the element wherein a combination of an antibody (antigen) and a labelled antigen (labelled antibody) is used essentially. The antibody (antigen) is combined with a first matrix and is immobilzed by a carrier not to be releaseable in water. The labelled antigen (labelled antibody) is combined with a second matrix and may be released in water.

PRIOR ART STATEMENT

A variety of immunoassays has hitherto been well-known in the art, wherein an analyte (i.e. a component to be analysed or an objective material to be analysed), such as drugs contained in blood or other body fluids, internal secretions (hormones, peptides, etc.) and proteins, is determined by the utilization of an antigen-antibody reaction (which may be referred to generally as "immunoreaction") from the prior art references, some of which will be listed below.

References relating to general immunoassay technology:

Kiyoshi Miyai, "BUNSEKI" ("Analysis"), 1985, pages 79 to 88; and

"Extra Number Issue of Japanese Journal of Clinical Pathology", No. 53 (1983).

References relating to enzyme immunoassay:

D. Monroe, "Analytical Chemistry", 56, 920A–931A (1984); and

Eiji Ishikawa et al, "KOSO-MENEKI SOKUTEIHO" ("Enzyme Immunoassay"), second edition (published by IGAKU SHOIN in 1982).

References relating to fluorecent immunoassay:

Fukuko Watanabe, "KENSA-TO-GIJUTU" ("Examination & Technology"), 9, pages 538 to 578 (1981);

I. Hemmilae, "Clinical Chemistry", 31, pages 359 to 370 (1985)

There is also found, for example, the following reference which describes the analytical method for determining the concentration of drugs in blood, the immunoassay being applied therein:

Ikuo Johno, "PHARMACIA", 21, pages 126 to 132 (1985)

The desirable determination method which is excellent in sensitivity among the aforelisted immunoassays, is a competitive heterogeneous immunoassay wherein an antigen or antibody labelled with a marker, such as an enzyme or fluorescent material. However, all of the known processes, as referred to above, are wet type processes. That is, they are the processes in which aqueous solutions are used. In detail, they are the processes wherein operations for handling aqueous solutions are involved throughout the assay operations, for example, the reaction solution being subjected to measurement of the labelling marker directed after the completion of the antigen-antibody reaction directly in the solution state. For this reason, complicated operations including preparation, weighing and storage of the reagent are required, in addition to complicated operations such as spectrophotometry.

The operations become further complicated, since it is required to separate the bound (hereinafter referred to as "B") of the antigen-antibody reaction from the free labelled body (hereinafter referred to as "F"), for example, by centrifugal separation or filtration.

In order to eliminate the in situ preparation and weighing of a reagent solution, it has been tried to supply the measuring reagent in the dry state. Reagent compositions required in analysis may be used in dry state, the typical example being dry type analysis elements in the form of a tablet containing a certain biochemical test composition or filter paper impregnated with a certain biochemical test composition, which is disclosed, for example, by Japanese Patent Publication No. 8850/1956, Japanese Patent Laid-Open publication Nos. 84963/1973, 62561/1983 and 97056/1984 and German DT-OS 3 048 799. However, even if any one of the known processes is applied to immunoassay, the complex and troublesome B/F separation operation could not be dispensed since the only obtainable effect is nothing but that the all of the ingredients contained in the reagent are easily dissloved.

In the field of immunoassay, a so-called solid phase immnunoassay is well known by the following prior references, in which, in order to facilitate the B/F separation, the antibody is immobilized on the surface of beads, on the internal wall surface of a test tube or included in microcapsules.

Kiyoshi Miyai, "Journal of Medical Technology", 22, pages 1219 to 1229 (1978).

Ikuo Johno, "Phamacia", 21, pages 126–132 (1985);

Yoneda et al, "The Journal of Clinical Laboratory Instruments and Reagents", 8, pages 1283 to 1289 (1985);

E P. Halpern et al, "Clinical Chemistry", 25, pages 1561 to 1563 (1979); and

G. Samuel et al, "Clinical Chemistry", 25, pages 168–170 (1983).

However, the processes known by the aforelisted prior art references are no more than the ones by which the B/F separation is simplified by immobilizing either one of the antigen or antibody and separating the solid phase containing the formed antigen-antibody complex from the sample solution. The other components of the reagent are supplied while being contained in an aqueous solution, with the measuring operation of the marker is conducted in wet system (aqueous solution system). It leads to the result that weighing of the reagent cannot be dispensed in preparation of the reagent solution and that storage and handling of the reagent solution is relatively troublesome. Accordingly, it is hard to say that that these processes are simplified ones.

"Clinical Chemistry", 31, pages 910–911 (1985) discloses a dry type multi-layered enzyme immunoassay element for clinical examination of drug concentration in serum. In this known element (used for analysis; hereinafter referred to as analysis element), an antibody is immobilized in a layer thereof and a labelled antigen is fed together with an antigen while being contained in an aqueous solution. In this analysis element system, antibodies for individual analyte drugs should be incorporated. And thus, different kinds of elements must be prepared and used to analyse respective drugs, leading to the result that the number of elements becomes large.

OBJECT AND SUMMARY OF THE INVENTION

A primary object of this invention is to improve the existing competitive binding assay-heterogeneous system.

Another object of this invention is to provide an immunoassay element and an immunoassay process utilizing the element, wherein complicated operations necessary in the existing competitive binding assay-heterogeneous system can be obviated.

A more specific object of this invention is to provide an immunoassay element and an immunoassay process utilizing the element, wherein an analyte antigen substance (antibody substance) is analysed by a simplified dry operation while eliminating the operations for preparing and weighing the reagent and the complex and troublesome B/F separation.

According to a first aspect of this invention, there is provided element for the quantitative analysis of an analyte antigen contained in an aqueous liquid sample, comprising:

a first matrix for retaining a carrier so that said carrier is not released in said aqueous liquid sample, said carrier immobilizing an antibody for said analyte antigen; and a second matrix for retaining a marker-labelled antigen so that said marker-labelled antigen is dissolved or otherwise released in said aqueous liquid sample upon contact with said aqueous liquid sample;

whereby said marker-labelled antigen reacts with said immobilized antibody in competition with the antigen-antibody reaction between said said analyte antigen and said immobilized antibody.

According to a second aspect of this invention, there is provided a combination of first and second elements for quantitative analysis of an analyte antigen contained in an aqueous liquid sample, wherein said first element includes a first matrix for retaining a carrier so that said carrier is not released in said aqueous liquid sample, said carrier immobilizing an antibody for said analyte antigen, and a second element includes a second matrix for retaining a marker-labelled antigen so that said marker-labelled antigen is dissolved or otherwise released in said aqueous liquid sample upon contact with said aqueous liquid sample, said first element being immersed in said aqueous liquid sample to allow said analyte antigen to react with the immobilized antibody, and said second element being immersed in said aqueous liquid sample after the completion of the reaction between the analyte antigen and the immobilized antibody to allow the marker-labelled antigen to react with the remaining immobilized antibody.

According to a third aspect of this invention, there is provided a process for the quantitative analysis of an analyte antigen contained in an aqueous liquid sample, wherein said analyte antigen reacts with an immobilized antibody in competition with the reaction between an antigen labelled with a marker and said immobilized antibody, and wherein the quantity of said marker labelling to the labelled antigen which is combined with said immobilized antibody is determined, comprising the steps of:

(a) immersing an element for the quantitative analysis of said analyte antigen in an aqueous liquid sample; said element including a first matrix for retaining a carrier so that said carrier is not released in said aqueous liquid sample, said carrier immobilizing an antibody for said analyte antigen; and a second matrix for retaining a marker-labelled antigen so that said marker-labelled antigen is dissolved or otherwise released in said aqueous liquid sample upon contact with said aqueous liquid sample;

whereby said marker-labelled antigen reacts with said immobilized antibody in competition with the antigen-antibody reaction between said analyte antigen and said immobilized antibody so that only the portion of the immobilized antibody which has not been combined with said analyte antigen is combined with said marker-labelled antigen;

(b) removing said first matrix from said aqueous liquid sample after the completion of the competitive antigen-antibody reactions; and (c) determining the quantity of labelling marker in the marker-labelled antigen combined with said immobilized antibody.

According to a fourth aspect of this invention, there is provided a process for the quantitative analysis of an analyte antigen contained in an aqueous liquid sample, wherein said analyte antigen reacts with an immobilized antibody in competition with the reaction between an antigen labelled with a marker and said immobilized antibody, and wherein the quantity of said marker labelling to the free labelled antigen which has not been combined with immobilized antibody is determined, comprising the steps of:

(a) immersing an element for the quantitative analysis of said analyte antigen in an aqueous liquid sample; said element including a first matrix for retaining a carrier so that said carrier is not released in said aqueous liquid sample, said carrier immobilizing an antibody for said analyte antigen; and a second matrix for retaining a marker-labelled antigen so that said marker-labelled antigen is dissolved or otherwise released in said aqueous liquid sample upon contact with said aqueous liquid sample;

whereby said marker-labelled antigen reacts with said immobilized antibody in competition with the antigen-antibody reaction between said analyte antigen and said immobilized antibody so that only the portion of the marker-labelled antigen which has not been combined with said immobilized antibody is left in said aqueous liquid sample; and (b) determining the quantity of labelling marker left in said aqueous liquid sample after the completion of the competitive antigen-antibody reactions.

The measuring step (b) in the process for the quantitative analysis of an analyte antigen contained in an aqueous liquid sample provided in accordance with the fourth aspect, is effected by the use of a dry analytical element.

The analyte antigen in all of the elements and/or processes according to the first to fourth aspect of this invention may be substituted replaced by analyte antibody, with the antibody immobilized by the carrier being replaced by an antigen, so that fifth to eighth embodiments of this invention is provided.

The immnunoanalytical element, according to this invention, is an element (or molded mass) containing a dry immuno-reagent composition which is essentially consisting of an antibody immobilizing matrix (this being referred to as "first matrix" in the appended claims and in most portion of the specification) and a labelling antigen retaining matrix (this being referred to as "second matrix" in the appended claims and in most portion of the specifiation). Meantime, the term "dry" used in this specification means the condition or state ranging from the substantially dried state (wherein immuno-reagent composition is contained in the element for analysis under a substantially dry state or condition) to the apparent dried state (wherein immuno-reagent composition is contained in the element for analysis under a semi-dried state or contained is a concentrated aqueous solution but the aqueous solution containing the immnuno-reagent composition is not handled during the analysis operation). In dry analysis operation, any aqueous solution need not be handled after a sample in the form of an aqueous liquid or solution has been dripped or spotted in or on the element used for analysis.

The antigens and antibodies contained in the immuno-reagent of this invention include ordinary antigens and antibodies, and antigen-like or antibody-like substances within a broad range such as low molecular weight compounds (haptens), receptors, complements and virus. In other words, the term "antigen and antibody" used throughout the specification and claims should be interpreted to have the broadest meaning provided that the combination or coupling thereof exhibits a specific mutual affinity. The terms "labelled antigens" and "labelled antibodies" means antigens and antibodies directly or indirectly labelled with markers with the aim to realizing convenient quantitative analysis relating to the contents or quantities of the uncoupled antigens and antibodies remaining after the completion of the antigen-antibody reaction. Markers conveniently used for such purpose may be selected from the known markers including enzymes, coenzymes, fluorescent materials and dyes. These labelled antigens (or antibodies) have specific mutual affinities with the opponent antibodies (or antigens) similar to the antigens (or antibodies) which have not been labelled.

DESCRIPTION OF THE DRAWINGS

Presently preferred embodiments of the elements for immunoassay and mode of use thereof are shown in the appended drawings, in which.

DESCRIPTION OF PREFERRED EMBODIMENT

Preferred embodiments of the present invention will now be described in detail.

Figure 1:
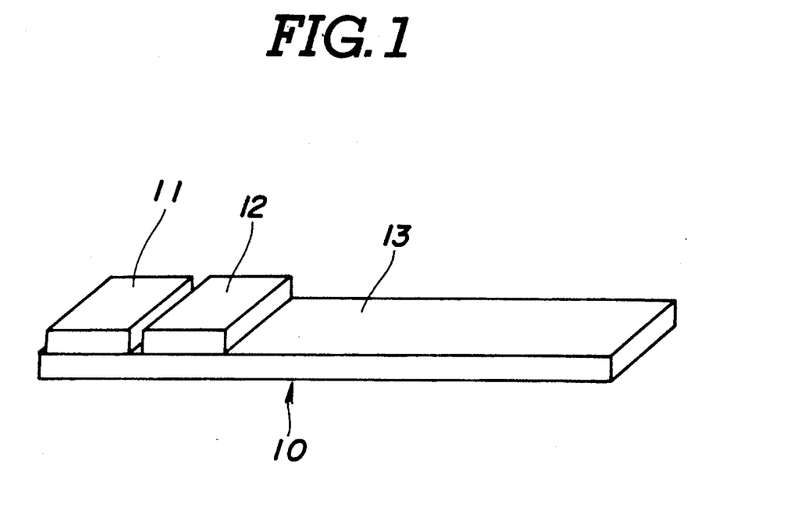
FIGS. 1 to 4 show embodiments of the elements for immunoassay, wherein four type test strips are illustratively shown.
Figure 5:
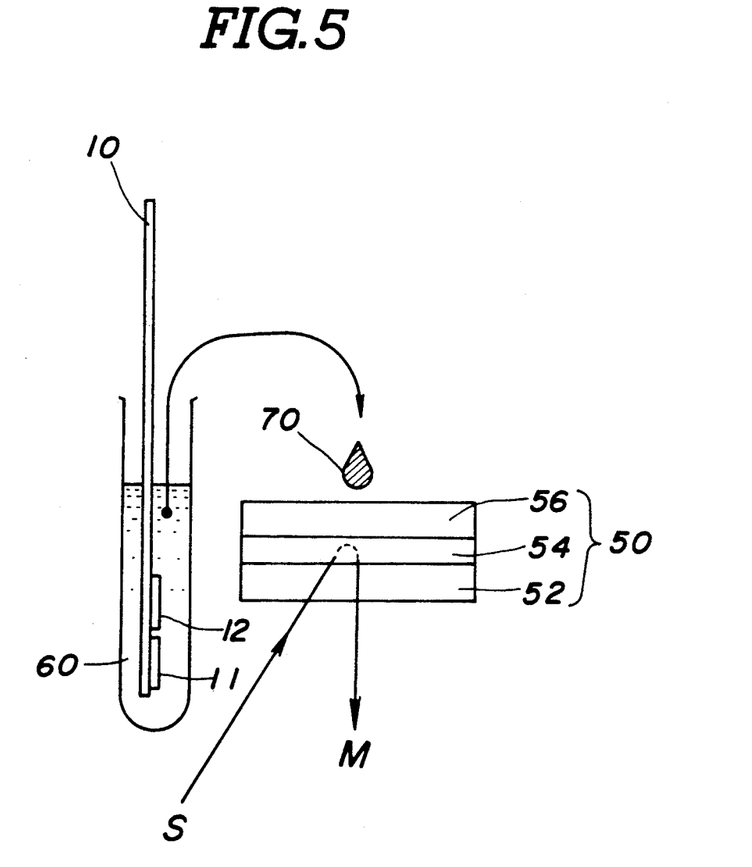
FIG. 5 is a diagrammatical view showing the sequential steps of a process for quantitative analysis of an antigen, according to this invention, wherein an embodiment of this invention is used in combination of a integral multi-layered analysis element for the analysis of the marker.

In the appended drawings, FIG. 1 is a perspective view showing schematically an embodiment of the element for quantitative analysis of an immunoreactive analyte according to this invention; and FIG. 5 is a sketch showing schematically the process for quantitative analysis wherein the element of FIG. 1 is used.

Referring to FIGS. 1 and 5 in combination, an embodiment of the element for immunoassay is denoted generally by reference numeral 10 and has a strip or web-like shape. The strip 10 comprises a support 13, and an antibody immobilizing matrix 11 (referred to as "first matrix" in the claims and some portions of the specification) and a labelled antigen retaining matrix 12 (referred to as "second matrix" in the claims and some portions of the specification) juxtaposed on the support 13.

The antibody immobilizing matrix 11 contains a carrier for immobilizing an antibody for the analyte antigen so that the antibody can readily contact with the components in the aqueous sample solution but the antibody is never released or dissolved in the aqueous sample solution. The matrix 11 provides a field or domain in which a competitive antigen-antibody binding reactions between three members of an antigen, a labelled antigen and a common antibody therefor take place, and has a function of retaining the antigen-antibody complex (B) and the labelled antigen-antibody complex (B) so that they are not dissolved in water. This leads to the result that both of these complexes are present only in the matrix 11 with the unreacted free labelled antigen (F) is present in water, whereby B/F separation is effected without any particular operations or steps purposely incorporated.

Any known carriers may be used, as long as they contain no ingredients harmful to antigen-antibody reaction or the harmful ingredients or matters are not released even if such matters might be contained. Exemplary materials for the carrier include granulated, globular and plate-shaped plastics, glass, fibers and gelled materials.

On the other hand, examples of the material for the matrix which contains the carrier for the immunoreactive substance (i.e. the antibody in this instance) are micro-porous sheet-shaped materials, such as filter paper made of natural or synthetic polymer fibers, non-woven fiber cloth, micro-porous sheet dispersed therein with micro particles, polymer films having binder surfaces, and membrane filters. The carrier may be laminated with or mixed internally in the matrix.

Alternatively, the antibody may be immobilized in the matrix per se so that the matrix is utilized as the carrier. In such a case, it is preferable to use a material having a large specific surface and selected from the materials including filter paper made of natural or synthetic polymer fibers, non-woven fiber cloth, micro-porous sheet including micro particles, polymer films having binder surfaces, and membrane filters.

The antibody may be immobilized by any known method for immobilization thereof. For example, when the antibody is immobilized by filter paper, it may be immobilized by the use of filter paper activated by BrCN as described in the specification of Japanese Patent Laid-Open Publication No. 200862/1982. The filter paper is cut to prepare a filter paper piece to be used as an element for one time test. Otherwise, a filter paper piece having a proper area is prepared, and a constant volumes for a time of an antibody and labelled antigen are dropped on separate sheets of paper, or on a single sheet of paper at separate positions, followed by drying. Strip- or sheet-shape paper is preferred since the preparation and storage of such sheets may be conducted in the manner employed for the preparation and storage of the conventional test strips used as the elements for biochemical tests.

The labelled antigen retaining matrix 12 (referred to as "second matrix" in the claims and some portions of the specification) retains a labelled antigen, which has been labelled with an appropriate marker suited for the subsequent operation, so that the labelled antigen is dissolved or released in an aqueous sample solution. Accordingly, the labelled antigen is retained in the matrix (second matrix) only tentatively and can be dissolved in aqueous solution rapidly by immersing the matrix in the solution. Such a matrix may be prepared generally following to the preparation procedure disclosed, for example, by Japanese Patent Publication No. 8850/1956, Japanese Patent Laid-Open Publication Nos. 84963/1973, 62561/1983 and 97056/1984, and German DT-OS 3 048 799, and thus more favorable than the reagent of wet type single vial system in respect of the volume, accuracy, starting materials used, steps necessary for the preparations thereof.

Similar to the aforesaid antibody immobilizing matrix 11, the labelled antigen may be retained by a carrier contained in the matrix 12. However, it is necessary to take some measure so that the labelled antigen can be easily dissolved or released. In case where a labelled antigen is retained by filter paper, a recommendable process comprises the step of immersing the filter paper in an aqueous solution containing the labelled antigen and a hydrophilic polymer binder which is easily soluble in water, such as gelatin or poly-N-vinylpyrrolidone, followed by the step of pulling the filter paper from the solution, the step of drying to form a dry sheet by any proper drying method, for example by lyophilizing or drying at a low temperature, and the step of cutting to obtain cut sheet pieces or strips. The labelled antigen retaining sheet, prepared in accordance with the aforementioned process, releases the labelled antigen readily within the normal analysis time.

The immuno-reagent composition formed by the combination of the components retained by the antibody immobilizing matrix and the labelled antigen retaining matrix may be selected to suit for the analysis of the analyte antigen to be analysed.

Although the embodiment has been described while referring to an example utilizing a combination of an antibody immobilizing matrix and a labelled antigen retaining matrix in the foregoing description; a combination of an antigen immobilizing matrix for immobilizing an antigen and a labelled antibody retaining matrix which retains the labelled antibody in the easily releaseable condition may be used when an antibody is the analyte to be analysed quantitatively. Although further description of such the combination will be omitted for simplification of the specification, the present invention include many such combinations within the scope thereof.

Meanwhile, reference numeral 50 in FIG. 5 designates a dry type marker analysis element. In this connection, the term "dry type marker analysis element" means elements for analysis capable of measuring or determining the amounts of the labelled antigens while the markers bound therewith are utilized as the indices; more specifically it means, for example, a multi-layered analysis element having a filter paper or test strip impregnated with a reagent composition required for the quantitative analysis of the marker or the reagent composition internally of either of the layers. Such a marker analysis element is disclosed, for example, B. Walter, "Analytical Chemistry", 55 498A–514A (1983) and J. N. Eikenberry, "Clinical Chemistry", 29, 1247 (1983). By the use of such a analysis element, a reaction utilized for the analysis proceeds in the element only by applying or spotting an aqueous solution of a labelled antigen to give the result showing the quantity or content of the marker. Many antigens may be analysed quantitatively by a single analysis element when a common marker is bound for labelling to different immunoreactive components (i.e. antigens when the antigens, are the analytes) irrespective of the binding specificity of the analyte antigen to be analysed specifically by a certain process.

As a merit, the device used for the quantitative analysis may be simplified.

As a typical example of the dry type marker analysis element for the quantitative analysis of a free labelled antigen, it will be mentioned to a multi-layered element for quantitative analysis. Assuming now that the marker is glucose peroxidase (GOD), the multi-layered element may include a GOD activity measuring coloring reagents which contain glucose (substrate), peroxidase, a tetramethylbenzidine leuco dye, and a pH buffer in order that the element has a capability of measuring the GOD activity. In this example, the leuco dye may be replaced by a combination of a pigment such as 4-aminoantipyrine or a derivative thereof with a coupler selected from derivatives of naphthol including 2,7-dihydroxynaphthalene, 3,5-dichloro-2-hydroxybenzenesulfonic acid or phenols.

When an enzyme is used as the marker labelling to the antigen, the examples of such enzyme being alkaline phosphatase (ALP), glucose-6-phosphate dehydrogenase (G6PDH) and galactose oxidase, an analysis element containing a reagent composition suited for the determination of the individual enzyme is used. When a fluorescent substrate is used as the enzyme substrate, the quantitative analysis may be conducted through the known fluorophotometry disclosed, for example, J. L. Giegel et al, "Clinical Chemistry", 28, pages 1894 to 1898 (1982).

One specific example, which may be used as the multi-layered element for quantitative analysis of a marker, comprises a transparent water-impermeable support, and at least two layers applied on the support, the said two layer being a coloring reagent layer containing a coloring reagent composition dispered in a hydrophilic polymer binder represented by gelatine and applied to cover the support, and a porous spreading layer covering the coloring reagent layer. Such an element may be selected from those disclosed by Japanese Patent Laid-Open Publication Nos. 164356/1980, 66359/1982, 222769/1985, 148250/1982 and 125847/1982, Japanese Patent Publication No. 21677/1978, U.S. Pat. No. 3,992,158 and Japanese Patent Laid-Open Publication Nos. 90859/1980 and 4959/1986. A further example of such an integral multi-layered analysis element comprises a transparent water-impermeable support, a water-absorbing layer mainly composed of a hydrophilic polymer binder, such as gelatine or polyvinyl alcohol covering the support, and a porous reagent spreading layer containing a coloring reagent composition dispersed or impregnated therein and covering the water-absorbing layer. Examples thereof may be found in Japanese Patent Laid-Open Publication Nos. 12095/1984, 222769/1985, 222760/1985 and 41967/1986.

A still further embodiment of an integral multi-layered analysis element comprises a transparent water-impermeable support, a detection layer laminated on the support to cover the same, and a porous reagent spreading layer containing a coloring reagent composition dispersed or impregnated therein and covering the detection layer, said detection layer containing gelatine as a main ingredient, or containing a polymer mordant as a main ingredient, or said detection layer being comprised of a hydrophilic polymer binder, such as gelatine or polyvinyl alcohol, and a mordant or polymer mordant contained in the binder. Example thereof may be found in Japanese Patent Laid-Open Publication Nos.

12095/1984, 222769/1985, 222760/1985 and 41967/1986 and Japanese Patent Publication No. 18628/1983.

The marker analysis element 50, according to the first embodiment of this invention, is an integral laminated sheet comprising a top reagent spreading layer 56 containing said reagent composition, a water-absorbing layer 54 which acts also as a detection layer and underlaid beneath the top reagent spreading layer, and a base transparent water-impermeable support 52 underlaid beneath the water-absorbing layer. In analytical operation by the use of this embodiment, a solution denoted by 70 and containing free labelled antigen which has not bound with the antibody during the competitive antigen-antibody reaction is spotted on the spreading layer 56, whereby a dye is formed in an amount in some quantitative interrelation with the amount of the labelled antigen, and then the optical density of the thus formed dye is measured by reflective photometry. As seen from FIG. 5, the optical density of the reflected light is measured from the side of the transparent support 52, by irradiating the marker analysis element 50 with the light from the light source S and the reflected light is measured using a photomultiplier M.

The operations in quantitative analysis of immunoreactive material in accordance with this embodiment will now be described.

In case where an antigen in an aqueous sample solution is quantitatively analysed, the sample solution is diluted to have an appropriate concentration and a predetermined volume of the solution is put into a test tube. A strip 10 having an antibody immobilizing matrix 12 and a labelled antigen retaining matrix 13 is immersed in the test tube 60, followed by incubation for a predetermined time under agitation. Then, a predetermined amount of the solution in the test tube 60 is spotted on the marker analysis element 50, as denoted by a droplet 70. Since the coloring optical density in the analysis element 50 is in some interrelation with the amount or content of antigen in the aqueous sample solution, it is possible to know the quantity or content of the antigen in the aqueous sample solution by measuring the optical density and processed through the principle of colorimetry. Whereas the marker labelling to the residual free labelled antigen which has not participated in the reaction during the antigen-antibody reaction (immunoreaction) is determined to analyse the antigen quantitatively, it may be also possible to quantitatively analyse an antigen by using the marker in the reaction product of the antigen-antibody reaction, i.e. the antigen-antibody bound, formed in the antibody immobilizing matrix is used as an indicator. As will be apparent to those skilled in the art, by using the element for immunoreactive analysis of this invention, the operator conducting the analytical operation can easily proceed the analysis of immunoreactive materials without the need of complicated operations in preparation, weighing and B/F separation; and when a dry system marker analysis element is used together, a variety of antigens and antibodies can be easily tested while being kept dry throughout the overall process including the colorimetric measuring step.

Figure 2:
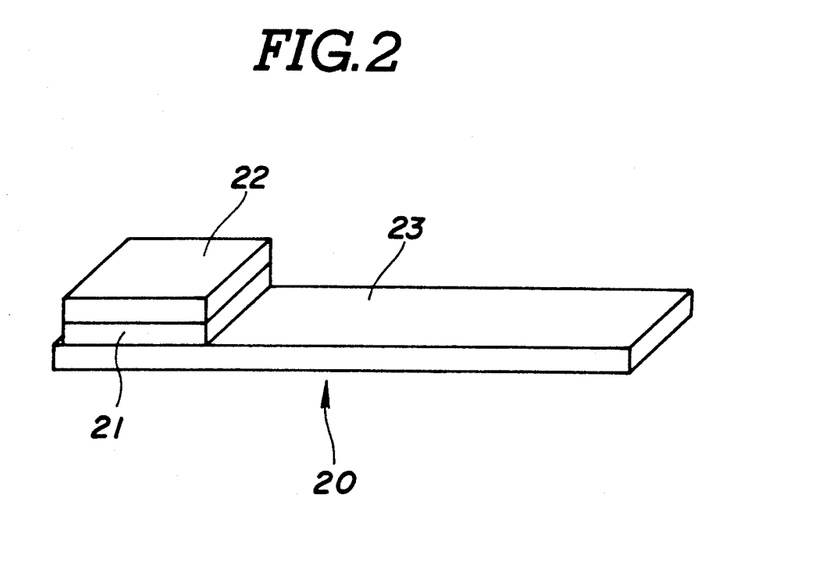

Although the antibody immobilizing matrix 12 and the labelled antigen retaining matrix 13 are juxtaposed on the support 11 in the aforementioned embodiment, the element for quantitative analysis of this invention may be in the form of a strip 20 comprising a support 23 and a laminate of an antibody immobilizing matrix 21 and a labelled antigen retaining matrix 22 laid on or laminated with the support 23, as shown by the embodiment in FIG. 2. However, in this embodiment, the laminate should be prepared under dried condition and stored as a dry sheet until the commencement of the analytical operation to obviate contact of both reagent components, i.e. the antibody and the labelled antigen.

Figure 3:
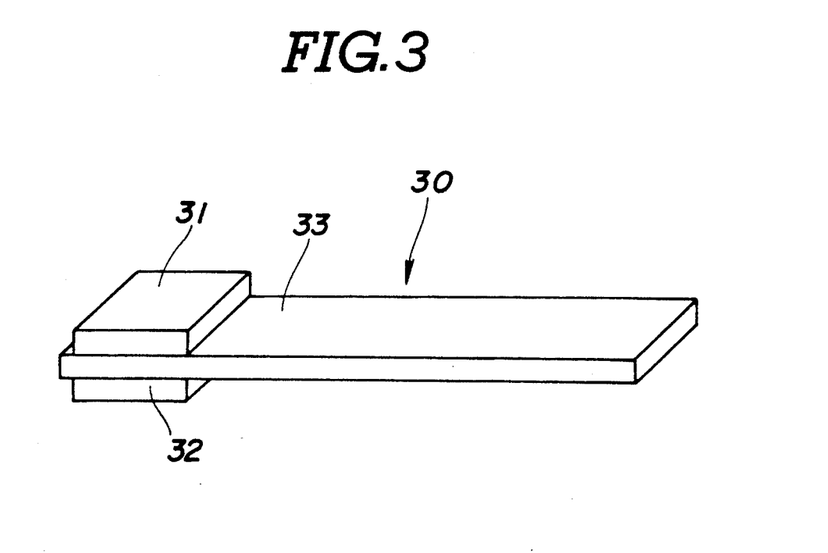

A third embodiment is shown in FIG. 3, wherein an element for immunoassay is shown in the form of a strip 30 comprising an antibody immobilizing matrix 31 and a labelled antigen retaining matrix 32 applied on both sides of a support 33.

Figure 4:
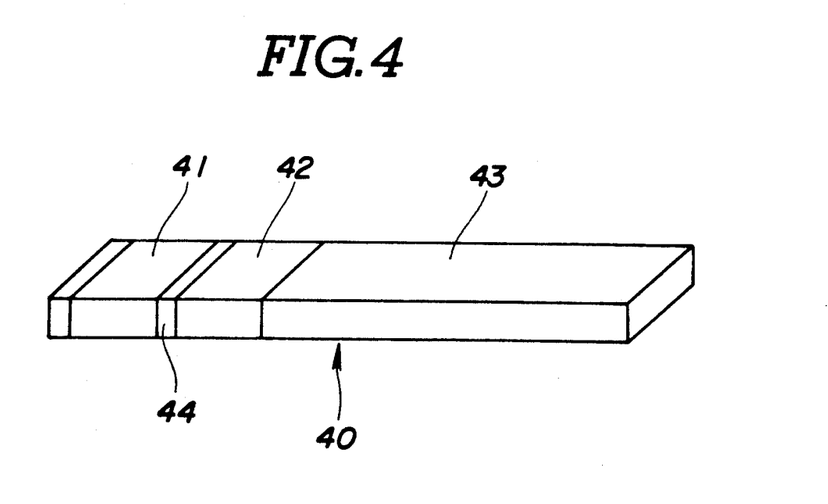

A fourth embodiment is shown in FIG. 4, wherein a strip 40 serving as the element for immunoassay according to this invention comprises a support 43 formed of a matrix, such as filter paper, and having an antibody immobilizing matrix zone 41 formed by immersing an antibody directly at the portion of the support 43 to be impregnated with the antibody, and a labelled antigen retaining zone 42 impregnated with a labelled antigen in a silimar manner. It is recommendable to use a porous body as the support 43 which is provided with water-impermeable barrier bands 44 to exclude the possibility that both of the reagent components are not mixed with each other during the step of preparing this embodiment.

Although the embodiments described above are in the shape of a strip having a portion which is to be pinched and/or held by the fingers of the user, the element for quantitative analysis for immunoreactive material, according to the present invention, is not limited only to such shape but may be in the form of a simple sheet or rectangular parallelepiped block which is to be put into a test tube or an aqueous sample solution. However, the strip-shaped embodiments are preferred, since they have the portions which allow easy access by the user's fingers for simpler handling. As an additional merit, the operation is simplified, since a single strip having an antibody immobilizing matrix and a labelled antigen retaining matrix is used so that both matrices are put into the aqueous sample solution concurrently.

As a further different form, the antibody may be immobilized on the surfaces of beads or inner wall surface of a test tube, the labelled antigen being retained by a sheet piece of filter paper or the like, or the vice versa combination.

Although all of the aforementioned embodiments are elements for quantitative analysis of immunoreactive materials partipitating in competitive reactions, the broad concept of this invention may be applied in a noncompetitive binding assay or a sequential saturation technique disclosed by A. Zettner et al, "Clinical Chemistry", 20, pages 5 to 14 (1974). For example, in a noncompetitive binding assay, an antibody immobilizing materix is first put into an aqueous sample solution to allow all of the analyte antigen to bind with the immobilized antibody, and then a labelled antigen retaining matrix is put into the same aqueous sample liquid to allow the labelled antigen to bind or couple with the residing immobilized antibody which has not been bound with the analyte antigen in the preceding operation.

EXAMPLE OF THE INVENTION

An example of the process for quantitative analysis of an antigen in an aqueous sample solution while utilizing the element of this invention, it will be described an example wherein the concentration of Theophylline in a blood serum is analysed. In this Example, Theophylline is an analyte antigen.

Reaction

Glucose + $O_2$ + $H_2O \longrightarrow H_2O_2$ + Gluconate

Peroxidase

Leuco Dye + $H_2O_2 \longrightarrow$ Dye

Reagent and Immunoassay Element

A test strip-shaped element 10 shown in FIG. 1 is used, the test strip being composed of a support 13 in the form of a rectangular strip applied with a sheet piece 11 in which anti-Theophylline is immobilized and a sheet piece 12 retaining Theophylline labelled by GOD. A marker analysis element 50 shown at the right side of FIG. 5 is used as a multi-layered analysis element for quantitative analysis of GOD.

Process of Analysis

As shown in FIG. 5, the strip 11 is immersed in 1 ml of a diluted blood serum contained in a test tube 60, and subjected to incubation for 5 minutes under agitation. 10 micro-liters of the solution in the test tube is picked up and spotted on the reagent spreading layer 56 of the multi-layered analysis element 50 for the determination of GOD as depicted by reference numeral 70, and then the optical density of coloring in the detection layer 54 of the element 50 is determined by reflective spectroscopy from the side of the support 52 while employing the rate method (kinetic method) or the end point method. The concentration of Theophylline in the diluted serum is calculated from the calibration curve.

The element for quantitative analysis of immunoreactive analyte and the process for analysing the analyte contained in an aqueous sample solution may be used for the quantitative analysis of wide variety of analyte immunoreactive materials, such as chemicals, hormones and proteins. The quantities of the reagents used in one time operation for quantitative analysis, namely the quantities of the antibody and the labelled antigen in this example, may be experimentally determined for individual antigens in view of the quantity of the antigen contained in the aqueous sample solution. The degree of dilution of the aqueous sample solution may be determined depending on the range of content of the analyte antigen.

As will be apparent from the foregoing, the element for immunoassay and the process for analysing the analyte may be particularly convenient when used for analysing quantitatively the content or quantity of an analyte antigen or antibody contained in an aqueous sample through a competitive and heterogeneous immunoassay. The merits of the present invention over the conventional wet type immunoassay using an aqueous solution containing a reagent composition for immunoanalysis will now be listed below for facilitating the understanding of the invention.

(1) Preparation and weighing of a test liquid is not needed.

(2) Complicated B/F separation, such as centrifugal separation or filtration, is dispensed.

(3) The analytical operations can be simplified since they are conducted through sequential operations under dry state.

(4) By adjusting the dilution rate of the aqueous sample depending on the content of analyte antigen (or antibody) contained therein, so that trace amount of analyte antigen (or antibody) can be analysed quantitatively.

(5) By using a common marker labelling to antigens corresponding to individual analyte antigens, only one kind of marker analysis element can be used for the analysis of labelled antigens, and thus the preparations and the device and analysis operations can be simplified and the costs required therefor are lowered.

(6) When a strip-shaped embodiment allow easy preparation, simplification of storage vessel, easy storage, easy handling, simplified analytical operations and simplification of construction of the instrument used for analysis, and cost for the preparation of the strip-shaped element is relatively low.

What is claimed is:

1. A process for the quantitative analysis of a sample antigen contained in an aqueous liquid sample wherein said sample antigen reacts with an immobilized antibody in competition with an antigen labelled with a marker in an antigen-immobilized antibody reaction, and wherein the quantity of said labelled antigen which has not combined with the immobilized antibody and which is a function of the concentration of said sample antigen is determined, comprising the steps of:

(a) immersing a dipstick analytical element into the aqueous liquid sample, said element comprising:
a first matrix,
a carrier in said first matrix containing immobilized antibody capable of immunochemical reaction with sample antigen wherein the immobilized antibody is not released into the aqueous liquid sample upon immersion therein; and, a second matrix containing labelled antigen and a hydrophilic polymer binder wherein the labelled antigen and the hydrophilic polymer binder dissolve in the aqueous liquid sample upon immersion therein to release said labelled antigen into said aqueous liquid sample;
whereby said labelled antigen reacts with said immobilized antibody in competition with said sample antigen in the antigen-immobilized antibody reaction between said sample antigen and said immobilized antibody, so that only that portion of the labelled antigen which has not combined with said immobilized antibody remains in said aqueous liquid sample; and (b) applying an aliquot of said aqueous liquid sample resulting from step (a) to a separate analytical element to determine the quantity of labelled antigen remaining in said aqueous liquid sample after the competition of the competitive antigen-immobilized antibody reactions and determining the amount of the sample antigen.

2. The process of claim 1 wherein said second matrix is composed of a filter paper containing the labelled antigen and a hydrophilic polymer binder.

3. A process for the quantitative analysis of a sample antibody contained in an aqueous liquid sample wherein said sample antibody reacts with an immobilized antigen in competition with an antibody labelled with a marker in an antibody-immobilized antigen reaction, and wherein the quantity of said labelled antibody which has not combined with the immobilized antigen and which is a function of the concentration of said sample antibody is determined, comprising the steps of;

(a) immersing a dipstick analytical element into the aqueous liquid sample, said element comprising:
a first matrix,
a carrier in said first matrix containing immobilized antigen capable of immunochemical reaction with sample antibody wherein the immobilized antigen is not released into the aqueous liquid sample upon immersion therein; and, a second matrix containing labelled antibody and a hydrophilic polymer binder wherein the labelled antibody and the hydrophilic polymer binder dissolve in the aqueous liquid sample upon immersion therein to release said labelled antibody into said aqueous liquid sample;

wherein said labelled antibody reacts with said immobilized antigen in competition with said sample antibody in the antibody-antigen reaction between said sample antibody and said immobilized antigen, so that only that portion of the labelled antibody which has not combined with said immobilized antibody remains in said aqueous liquid sample; and (b) applying an aliquot of said aqueous liquid sample resulting from step (a) to a separate analytical element to determine the quantity of labelled antibody remaining in said aqueous liquid sample after the completion of the competitive antibody immobilized antigen reactions.

4. The process of claim 3 wherein said second matrix is composed of a filter paper containing the labelled antibody and a hydrophilic polymer binder.

* * * * *